(12) United States Patent
Nagano et al.

(10) Patent No.: US 8,673,957 B2
(45) Date of Patent: Mar. 18, 2014

(54) FLUORESCENT PROBE

(75) Inventors: Tetsuo Nagano, Tokyo (JP); Yu Gabe, Tokyo (JP); Yasuteru Urano, Kanagawa (JP)

(73) Assignees: Tetsuo Nagano, Tokyo (JP); Daiichi Pure Chemicals Co., Ltd., Tokyo (JP)

( * ) Notice: Subject to any disclaimer, the term of this patent is extended or adjusted under 35 U.S.C. 154(b) by 0 days.

(21) Appl. No.: 13/425,802

(22) Filed: Mar. 21, 2012

(65) Prior Publication Data
US 2012/0178174 A1 Jul. 12, 2012

Related U.S. Application Data

(63) Continuation of application No. 12/688,625, filed on Jan. 15, 2010, now abandoned, which is a continuation of application No. 10/547,305, filed as application No. PCT/JP2004/002407 on Feb. 27, 2004, now abandoned.

(30) Foreign Application Priority Data

Feb. 28, 2003 (JP) ................... 2003-052256

(51) Int. Cl.
*A61K 31/40* (2006.01)
*C07D 209/56* (2006.01)

(52) U.S. Cl.
USPC ............ 514/411; 548/400; 548/405; 514/408

(58) Field of Classification Search
USPC ........................ 548/400, 405; 514/408, 411
See application file for complete search history.

(56) References Cited

U.S. PATENT DOCUMENTS

| | | | |
|---|---|---|---|
| 5,248,782 A | 9/1993 | Haugland et al. | |
| 5,874,590 A | 2/1999 | Nagano et al. | |
| 5,981,746 A | 11/1999 | Wolfbeis et al. | |
| 6,001,999 A | 12/1999 | Wolfbeis et al. | |
| 6,201,134 B1 | 3/2001 | Nagano et al. | |
| 7,897,786 B2 * | 3/2011 | Ulrich et al. | 548/405 |
| 8,258,171 B2 * | 9/2012 | Nagano et al. | 514/411 |
| 2009/0258434 A1 | 10/2009 | Nagano et al. | |
| 2010/0068733 A1 | 3/2010 | Nagano et al. | |

FOREIGN PATENT DOCUMENTS

| | | |
|---|---|---|
| JP | 10-338695 | 12/1998 |
| JP | 11-005796 | 1/1999 |
| JP | 2003-277385 | 10/2003 |

OTHER PUBLICATIONS

Gabe et al (2004): STN International HCAPLUS database, Columbus (OH), accession No. : 2004: 132539.*
K. Rurack et al., New J. Chem., vol. 25, pp. 289-292 (2001).
M. Wada et al., Tetrahedron Letters, vol. 42, pp. 6711-6713 (2001).
K. Rurack et al., Angew. Chem. Int. Ed., vol. 40, pp. 385-387 (2001).
J.H. Wiersma et al., Analytical Letters, vol. 3, pp. 123-132 (1970).
C.R. Sawicki, Analytical Letters, vol. 4, pp. 761-775 (1971).
P. Damiani et al., Talanta, vol. 33, pp. 649-652 (1986).
T.P. Misko et al., Anal. Biochem. vol. 214, pp. 11-16 (1993).
H. Maeda et al., J. Leuk. Biol., vol. 56, pp. 588-592 (1994).
T. Akaike et al., Biochemistry, vol. 32, pp. 827-832 (1993).
Organic Chemicals, Catalog 2004-2005, Tokyo Kasei Kogyo Co., Ltd., p. 665.
T. Nagano et al., Kagaku to Kyoiku (Chemistry and Education), vol. 47, pp. 665-669 (1999).
Ueno et al., Mechanism-Based Molecular Design of Highly Selective Fluorescence Probes for Nitrative Stress, 2006, Journal of the Chemical Society, 128, 10640-10641, (supporting information included).
Office Action, dated Nov. 29, 2010, in connection with U.S. Appl. No. 12/093,479 published as US 2009-0258434 A1.

* cited by examiner

*Primary Examiner* — Golam M M Shameem
(74) *Attorney, Agent, or Firm* — Greenblum & Bernstein, P.L.C.

(57) ABSTRACT

A compound represented by the formula (I) wherein $R^1$ and $R^2$ represent amino groups that substitute at adjacent positions on the benzene ring, wherein one of the amino groups may have one alkyl group; $R^3$ and $R^4$ represent hydrogen atom, a $C_{1-6}$ alkyl group, or a $C_{1-6}$ alkoxy group, $R^5$ and $R^8$ independently represent a $C_{1-6}$ alkyl group, $R^6$ and $R^9$ represent a carboxy-substituted $C_{1-6}$ alkyl group, an alkoxycarbonyl-substituted $C_{1-6}$ alkyl group, a sulfo-substituted $C_{1-6}$ alkyl group, or an alkyl sulfonate-substituted $C_{1-6}$ alkyl group, and $R^7$ and $R^{10}$ represent a $C_{1-6}$ alkyl group, an aryl group, a $C_{1-6}$ alkoxycarbonyl group, a vinyl group, a thienyl group, or a pyrrolyl group, and an agent for measurement of nitrogen monoxide containing the compound. Said compound can give a fluorescent substance that is free from change in fluorescence intensity in a wide pH range.

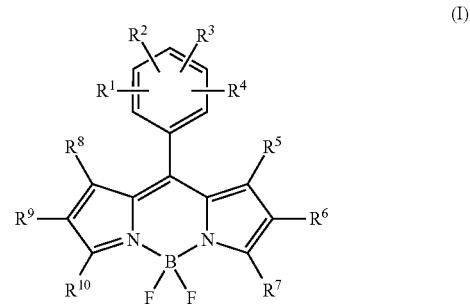

(I)

7 Claims, 2 Drawing Sheets

FLUORESCENT PROBE

CROSS-REFERENCE TO RELATED APPLICATIONS

This application is a continuation of application Ser. No. 12/688,625, filed Jan. 15, 2010, which is a continuation of application Ser. No. 10/547,305, now abandoned, which is the National Stage of International Application No. PCT/JP2004/002407, filed Feb. 27, 2004, which claims the benefit of Japanese Application No. 2003-052256 filed on Feb. 28, 2003. The disclosures of application Ser. Nos. 12/688,625, 10/547,305 and PCT/JP2004/002407 are expressly incorporated by reference herein in their entireties.

TECHNICAL FIELD

The present invention relates to a fluorescent probe. More specifically, the present invention relates to a fluorescent probe that captures nitrogen monoxide to emit fluorescence.

BACKGROUND ART

Recently, it has been reported that particular fluorescein derivatives that per se have almost no fluorescent property react with nitrogen monoxide under a neutral condition to provide a triazole compound having a strong fluorescence intensity, and the triazole derivative can emit intense fluorescence at wavelength of around 515 nm under excitation light at a long wavelength of around 495 nm (U.S. Pat. No. 5,874,590). When these fluorescein derivatives are used as an agent for nitrogen monoxide measurement, the excitation light can be easily cut off with a fluorescence filter provided on an ordinary fluorescence microscope, and intracellular nitrogen monoxide concentration can be conveniently measured by measuring fluorescence in individual cells.

Diaminorhodamine derivatives that can efficiently react with nitrogen monoxide under a neutral condition, and give a triazole derivative having superior fluorescence intensity have been proposed (U.S. Pat. No. 6,201,134). The fluorescence of the diaminorhodamine derivatives shifts to a longer wavelength side compared with the aforementioned fluorescein derivatives, thus the fluorescence does not substantially overlaps the auto fluorescence of cells, and the fluorescence does not attenuate even in an acidic region. Therefore, the fluorescence of the diaminorhodamine derivatives does not damage living tissues and cells, and enable measurement of nitrogen monoxide in a fluorescent region of a longer wavelength than in the auto fluorescent region of cells.

Indacene derivatives, which are known to have an ion capturing moiety useful for measurement of alkali metal ions or cations (Japanese Patent Laid-Open Publication (KOKAI) Nos. 10-338695 and 11-5796). However, no attempt has been reported for measurement of nitrogen monoxide by using the fluorescence chromophore of the indacene derivatives.

DISCLOSURE OF THE INVENTION

The inventors of the present invention conducted various researches to provide a fluorescent probe that specifically and efficiently captures nitrogen monoxide to emit fluorescence. As a result, they successfully provided an agent for nitrogen monoxide measurement that can efficiently react with nitrogen monoxide under a neutral condition to give a fluorescent substance having superior fluorescence intensity by using fluorescence chromophores of indacene derivatives (Japanese Patent Application No. 2002-80230).

The inventors of the present invention further conducted researches, and as a result, they found that an agent for nitrogen monoxide measurement further having superior water-solubility was successfully provided by introducing a substituent such as a carboxy-substituted alkyl group into the fluorescence chromophore of the indacene derivatives, and that an fluorescence intensity of the fluorescent triazole derivative, produced by trapping of nitrogen monoxide by the agent, was subjected to almost no influence by pH fluctuation. The present invention was achieved on the basis of these findings.

The present invention thus provides a compound represented by the following formula (I);

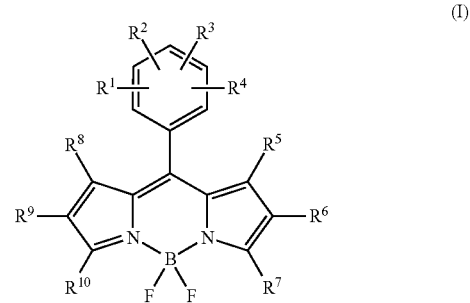

wherein, $R^1$ and $R^2$ represent amino groups that substitute at adjacent positions on the benzene ring, wherein one of the amino groups may have one alkyl group which may be substituted; $R^3$ and $R^4$ independently represent hydrogen atom, a $C_{1-6}$ alkyl group, or a $C_{1-6}$ alkoxy group, $R^5$ and $R^8$ independently represent a $C_{1-6}$ alkyl group which may be substituted, $R^6$ and $10$ independently represent a carboxy-substituted $C_{1-6}$ alkyl group, an alkoxycarbonyl-substituted $C_{1-6}$ alkyl group, a sulfo-substituted $C_{1-6}$ alkyl group, or an alkyl sulfonate-substituted $C_{1-6}$ alkyl group, and $R^7$ and $R^{10}$ independently represent a $C_{1-6}$ alkyl group which may be substituted, an aryl group which may be substituted, a $C_{1-6}$ alkoxycarbonyl group which may be substituted, a vinyl group which may be substituted, a thienyl group which may be substituted, or a pyrrolyl group which may be substituted, or a salt thereof.

According to a preferred embodiment of the present invention, the aforementioned compound or a salt thereof wherein $R^6$ and $R^9$ are 2-carboxy-1-ethyl groups, and $R^5$, $R^7$, $R^8$, and $R^{10}$ are methyl groups is provided. The present invention also provides an agent for measurement of nitrogen monoxide comprising the aforementioned compound or a salt thereof.

From another aspect, the present invention provides a compound represented by the following formula (II):

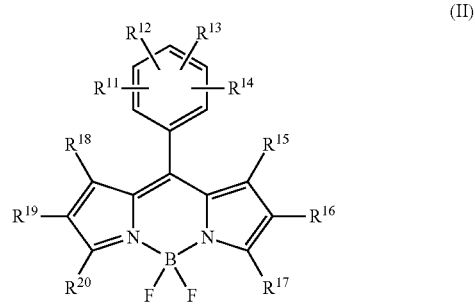

wherein, $R^{11}$ and $R^{12}$ combine together to represent a group represented by —N=N—$NR^{30}$— which forms a ring structure at adjacent positions on the benzene ring wherein $R^{30}$ represents hydrogen atom, or an alkyl group which may be substituted, or $R^{11}$ and $R^{12}$ represent a combination of an amino group (which may have an alkyl group which may be substituted or a protective group for amino group) and nitro group that substitute at adjacent positions on the benzene ring; $R^{13}$ and $R^{14}$ independently represent hydrogen atom, a $C_{1-6}$ alkyl group, or a $C_{1-6}$ alkoxy group, $R^{15}$ and $R^{18}$ independently represent a $C_{1-6}$ alkyl group which may be substituted, $R^{16}$ and $R^{19}$ independently represent a carboxy-substituted $C_{1-6}$ alkyl group, an alkoxycarbonyl-substituted $C_{1-6}$ alkyl group, a sulfo-substituted $C_{1-6}$ alkyl group, or an alkyl sulfonate-substituted $C_{1-6}$ alkyl group, and $R^{17}$ and $R^{20}$ independently represent a $C_{1-6}$ alkyl group which may be substituted, an aryl group which may be substituted, a $C_{1-6}$ alkoxycarbonyl group which may be substituted, a vinyl group which may be substituted, a thienyl group which may be substituted, or a pyrrolyl group which may be substituted, or a salt thereof. According to a preferred embodiment of the aforementioned invention, the compound or a salt thereof wherein $R^{16}$ and $R^{19}$ are 2-carboxy-1-ethyl groups, and $R^{15}$, $R^{17}$, $R^{18}$, and $R^{20}$ are methyl groups is provided.

From a further aspect, the present invention provides a method for measurement of nitrogen monoxide, which comprises the steps of (a) reacting a compound represented by the aforementioned formula (I) with nitrogen monoxide; and (b) detecting a compound represented by the aforementioned formula (II) produced in the aforementioned step (a) wherein $R^{11}$ and $R^{12}$ combine together to form a group represented by —N=N—$NR^{30}$— which forms a ring structure at adjacent positions on the benzene ring wherein $R^{30}$ represents hydrogen atom, or an alkyl group which may be substituted.

BEST MODE FOR CARRYING OUT THE INVENTION

Figure 1:
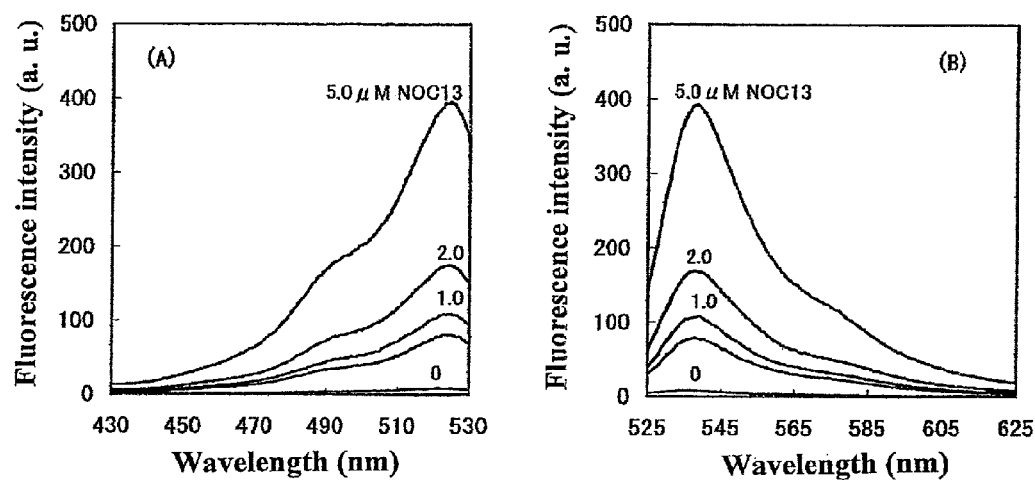
FIG. 1 shows the results of the measurement of changes of excitation and fluorescence spectra of Compound (7) after addition of NOC 13. In the drawing, (A) represent the excitation spectrum (Em: 535 nm), and (B) represents the fluorescence spectrum (Ex: 520 nm). The curves indicate the results for the NOC 13 concentrations of 5.0 µM, 2.0 µM, 1.0 µM, 0.5 µM, and 0 µM in the order that the fluorescence intensities shown by the curves decrease from the highest.

In the specification, the alkyl group may be a linear, branched, or cyclic alkyl group, or a combination thereof, unless otherwise specifically mentioned. An alkyl moiety of other substituents containing the alkyl moiety (e.g. alkoxy group) should be understood in the same manner. Further, when "which may be substituted" is referred to for a certain functional group, the type, number, and substitution position of the substituent are not particularly limited. The functional group may have, for example, a halogen atom (any of fluorine atom, chlorine atom, bromine atom, and iodine atom), hydroxy group, amino group, carboxy group, sulfo group, an alkyl sulfonate group, or the like as the substituent. Further, when the aryl group is referred to in the specification, the group may be either a monocyclic or polycyclic aryl group. Phenyl group can be preferably used. The aromatic ring should be understood in the same manner.

In the formula (I), when $R^3$ and/or $R^4$ represent a $C_{1-6}$ alkyl group, or a $C_{1-6}$ alkoxy group, it is preferred that these groups bind at the 2- and 6-position on the benzene ring. When these groups exist, the quantum yield and reaction rate may be improved, and thus detection sensitivity may sometimes be increased. As the alkyl group represented by $R^3$ or $R^4$, methyl group is preferred, and methoxy group is preferred as the alkoxy group. It is also preferred that both $R^3$ and $R^4$ are hydrogen atoms. $R^{13}$ and $R^{14}$ in the formula (II) should be understood in the same manner.

The carboxy-substituted $C_{1-6}$ alkyl group represented by $R^6$ or $R^9$ is preferably a monocarboxy-substituted $C_{1-6}$ alkyl group. The carbon number of the $C_{1-6}$ alkyl moiety of the carboxy-substituted $C_{1-6}$ alkyl group is preferably 1 to 4, more preferably 2 or 3, and most preferably 2. It is most preferred that $R^6$ and $R^9$ are 2-carboxy-1-ethyl groups. Examples of the alkoxycarbonyl-substituted $C_{1-6}$ alkyl group represented by $R^6$ or $R^9$ include a $C_{1-6}$ alkyl ester of the aforementioned carboxy-substituted $C_{1-6}$ alkyl group. Preferred examples include an ethoxycarbonyl-substituted $C_{1-6}$ alkyl group, and the like. As the sulfo-substituted $C_{1-6}$ alkyl group represented by $R^6$ or $R^9$, a monosulfo-substituted $C_{1-6}$ alkyl group is preferred. As the alkyl sulfonate-substituted $C_{1-6}$ alkyl group represented by $R^6$ or $R^9$, a monoalkyl sulfonate-substituted $C_{1-6}$ alkyl group is preferred. As the alkyl sulfonate group in the alkyl sulfonate-substituted $C_{1-6}$ alkyl group, a $C_{1-6}$ alkyl sulfonate ($C_{1-6}$ alkyl-O—$SO_2$—) is preferred. When $R^6$ and $R^9$ are monocarboxy-substituted $C_{1-6}$ alkyl groups, especially when $R^6$ and $R^9$ are 2-carboxy-1-ethyl groups, superior effects are obtained in that water-solubility of the compounds remarkably increases, and fluorescence intensity of the compounds represented by the formula (II) produced by a reaction with nitrogen monoxide is not subjected to influence of pH fluctuation.

As the aryl group represented by $R^7$ or $R^{10}$, a phenyl group is preferred. When the phenyl group has a substituent, sulfo group, a sulfonate group, and the like are preferred as the substituent, and a sulfo group is particularly preferred. As the $C_{1-6}$ alkoxycarbonyl group represented by $R^7$ or $R^{10}$, ethoxycarbonyl group is preferred. Examples of the substituent which exists on the vinyl group represented by $R^7$ or $R^{10}$ include a phenyl group, monoaminophenyl group, and a diaminophenyl group (for example, 3,4-diaminophenyl group). As the thienyl group or pyrrolyl group represented by $R^7$ or $R^{10}$, 2-thienyl group, or 2-pyrrolyl group is preferred, respectively. When $R^7$ and $R^{10}$ are groups other than alkyl group, fluorescence wavelength of the compounds may sometimes shift to a longer wavelength side.

In the formula (I), it is more preferred that $R^6$ and $R^9$ are 2-carboxy-1-ethyl groups. Further, in the formula (I), it is preferred that $R^5$, $R^7$, $R^8$, and $R^{10}$ are $C_{1-6}$ alkyl groups which may be substituted. For example, the compounds wherein $R^5$, $R^7$, $R^8$, and $R^{10}$ are methyl groups are preferred embodiments of the present invention. $R^{15}$, $R^{16}$, $R^{17}$, $R^{18}$, $R^{19}$, and $R^{20}$ in the formula (II) should be understood in the same manner as $R^5$, $R^6$, $R^7$, $R^8$, $R^9$, and $R^{10}$.

In the aforementioned formula (I), $R^1$ and $R^2$ represent amino groups that substitute at adjacent positions on the benzene ring. Both of $R^1$ and $R^2$ may be unsubstituted amino groups. Alternatively, either of $R^1$ and $R^2$ may be substituted with one alkyl group, and the alkyl group may have one or more substituents. Examples of the alkyl group which substitutes on the amino group include, for example, a linear or branched $C_{1-18}$ alkyl group (preferably a $C_{1-6}$ alkyl group). Specifically, for example, methyl group, ethyl group, n-propyl group, isopropyl group, n-butyl group, sec-butyl group, tert-butyl group and the like can be used. Examples of the alkyl group which has a substituent include, for example, a $C_{1-6}$ alkyl group substituted with a substituted or unsubstituted aryl group (aralkyl group) and the like. As the aryl-substituted alkyl group, for example, benzyl group, phenethyl group, paramethoxybenzyl group, paraethoxycarbonylbenzyl group, paracarboxybenzyl group, and the like can be used.

In the aforementioned formula (II), $R^{11}$ and $R^{12}$ combine together to represent a —N=N—NR$^{30}$— group which forms a ring structure at adjacent positions on the benzene ring. $R^{30}$ represents hydrogen atom, or an alkyl group which may be substituted. Examples of this alkyl group include a linear or branched $C_{1-18}$ alkyl group (preferably a $C_{1-6}$ alkyl group), and examples of the alkyl group which has a substituent include, for example, a substituted or unsubstituted aralkyl group. As the aralkyl group, for example, benzyl group, phenethyl group, paramethoxybenzyl group, paraethoxycarbonylbenzyl group, paracarboxybenzyl group, and the like can be used.

Further, $R^{11}$ and $R^{12}$ also represent a combination of an amino group (which may have one substituent) and nitro group that substitute at adjacent positions on the benzene ring, wherein either of $R^{11}$ and $R^{12}$ represents an amino group, and the other represents nitro group. The amino group represented by either $R^{11}$ or $R^{12}$ may be unsubstituted, or the group may have one alkyl group, for example, a $C_{1-18}$ alkyl group, preferably a $C_{1-6}$ alkyl group. Further, the alkyl group may be substituted, and for example, a substituted or unsubstituted aralkyl group or the like may substitute on the amino group. Moreover, the amino group may have a protective group for amino group, for example, an acyl group such as acetyl group, trifluoroacetyl group, and benzoyl group; an alkylsilyl group such as trimethylsilyl groups, or the like. An aralkyl group such as benzyl group may also be used as the protective group.

The compounds of the present invention represented by the formulas (I) and (II) may form a salt. Type of the salt is not particularly limited, and the salt may be an acid addition salt or base addition salt. Examples of the acid addition salt include mineral acid salts such as hydrochloride, sulfate, and nitrate, and organic acid salts such as methanesulfonate, citrate, p-toluenesulfonate, and oxalate. Examples of the base addition salt include metal salts such as sodium salt, potassium salt, and calcium salt, ammonium salts, and organic amine salts such as methylamine salt, and triethylamine salt. In addition, the compounds may form a salt with an amino acid such as glycine. However, salts of the compounds of the present invention are not limited to these specific examples.

The compounds of the present invention represented by the formula (I) or (II) may have one or more asymmetric carbon. Any of optical isomers in an optically pure form, arbitrary mixtures of optical isomers, racemates, diastereoisomers in a pure form, mixtures of diastereoisomers, and the like based on one or more asymmetric carbon atoms fall within the scope of the present invention. The compounds of the present invention may exist as hydrates or solvates, and it should be understood that these substances also fall within the scope of the present invention.

Among the compounds represented by the aforementioned formula (I), and the compounds represented by the aforementioned formula (II) wherein $R^{11}$ and $R^{12}$ represent a combination of an amino group and nitro group that substitute at adjacent positions on the benzene ring, those wherein $R^3$ and $R^4$ are hydrogen atoms, $R^6$ and $R^9$ are 2-carboxy-1-ethyl groups, and $R^5$, $R^7$, $R^8$, and $R^{10}$ are methyl groups, and those wherein $R^{13}$ and $R^{14}$ are hydrogen atoms, $R^{16}$ and $R^{19}$ are 2-carboxy-1-ethyl groups, and $R^{15}$, $R^{17}$, $R^{18}$, and $R^{20}$ are methyl groups, which are typical compounds, are specifically mentioned in the examples of the specification as for preparation examples thereof. Therefore, it will be understood that the compounds represented by the aforementioned formula (II) are useful as synthetic intermediates of the compounds represented by the formula (I). Among the compounds represented by the formula (II), the compounds wherein $R^{11}$ and $R^{12}$ combine together to represent the —N=N—NR$^{30}$— group, which forms a ring structure at adjacent positions on the phenyl ring, can be prepared by reacting a compound represented by the aforementioned formula (I) with nitrogen monoxide. These compounds have strong fluorescent property as described later, and are useful for measurement of nitrogen monoxide.

It will be understood by those skilled in the art that the compounds falling within the scope of the formula (I) or (II) can be easily produced by referring to the specific explanations of the examples of the specification. Further, synthetic methods of the indacene structure are mentioned in, for example, Japanese Patent Laid-Open Publication (KOKAI) Nos. 10-338695 and 11-5796, as well as in New J. Chem., 25, pp. 289-292, 2001; Tetrahedron Letters, 42, pp. 6711-6713, 2001; Angew. Chem. Int. Ed., 40 pp. 385-387, 2001; Japanese Patent Application No. 2002-80230, and the like, and therefore, those skilled in the art can prepare the compounds of the present invention still more easily by referring to these publications.

The compounds represented by the formula (I) of the present invention have a property that they efficiently react with nitrogen monoxide under a neutral condition and provide compounds of the formula (II) wherein $R^{11}$ and $R^{12}$ combine together to form the group —N=N—NR$^{30}$— which forms a ring structure at adjacent positions on the benzene ring in a good yield. The compounds represented by the formula (I), per se, emit almost no fluorescence when irradiated with excitation light of around 485 nm under a neutral condition, whereas the compounds of the above formula (II) have the property of emitting extremely strong fluorescence under the same condition. Therefore, nitrogen monoxide in living tissues or cells can be measured by introducing the compound represented by the formula (I) into a living tissue or a cell to allow the compound to react with nitrogen monoxide to form the fluorescent compound of the above formula (II), and measuring the fluorescence of the compound. In particular, the compounds of the formula (I) of the present invention have superior reactivity with nitrogen monoxide, and thus have an outstanding characteristic that they enable measurement of nitrogen monoxide with high sensitivity and accuracy.

The method for measurement of nitrogen monoxide provided by the present invention comprises the steps of reacting a compound represented by the above formula (I) with nitrogen monoxide to form a compound of formula (II), and measuring fluorescence of the compound of the formula (II) wherein $R^{11}$ and $R^{12}$ combine together to represent the —N=N—NR$^{30}$— group which forms a ring structure at adjacent positions on the benzene ring. The term "measurement" used in the specification should be construed in its broadest sense, which includes various measurement purposes such as, for example, detection, quantification, qualitative analysis and the like. The above reaction can preferably be carried out under a neutral condition, for example, in a range of from pH 6.0 to 8.0, preferably in a range of from pH 6.5 to 7.8, and more preferably in a range of from pH 6.8 to 7.6. However, the measurement of nitrogen monoxide using the compounds of the present invention is not limited to the measurements under the neutral range or weakly acidic range. For example, measurement can also be performed under a strongly acidic condition such as in gastric mucosal cells. In particular, the compounds represented by the formula (II) of the present invention have an extremely superior characteristic that fluorescence intensity does not change in a wide range of pH, and thus they enable accurate measurement without being influenced by pH fluctuation.

The measurement of fluorescence can be carried out according to a known fluorometry method (see, for example, Wiersma, J. H., Anal. Lett., 3, pp. 123-132, 1970; Sawicki, C. R., Anal. Lett., 4, pp. 761-775, 1971; Damiani, P. and Burini, G., Talanta, 8, pp. 649-652, 1986; Damiani, P. and Burini, G., Talanta, 8, pp. 649-652, 1986; and Misko, T. P., Anal. Biochem., 214, pp. 11-16, 1993, and the like). For the nitrogen monoxide measurement according to the present invention, for example, irradiation with light of about 520 nm as excitation light, and measurement of fluorescence of about 535 nm may preferably be performed. The compounds represented by the formula (II) of the present invention have a superior characteristic that they give sufficient fluorescence intensity even with an excitation light having a long wavelength, and therefore they can reduce damages on the living body, tissues, cells, and the like. Further, by using the light having such a wavelength, efficient cut off can be obtained by using a fluorescence filter provided on an ordinary fluorescence microscope, and measurement with high sensitivity can be achieved without using an unordinary filter.

Where particularly high sensitive measurement is required, the aforementioned measurement of nitrogen monoxide may be carried out in the presence of an oxygen source. As the oxygen source, for example, oxygen, ozone, oxide compounds or the like can be used. As the oxygen, dissolved oxygen can generally be used, and if desired, oxygen gas may be introduced into the reaction system, or an agent that can generate oxygen (e.g., hydrogen peroxide) may be added. The oxide compounds are not particularly limited so long as they have an oxide bond that can easily be cleaved, e.g., N—O, S—O, or P—O. For example, PTIO (2-phenyl-4,4,5,5-tetramethylimidazoline-1-oxyl-3-oxide, Maeda, H., et al., J. Leuk. Biol., 56, pp. 588-592, 1994; and Akaike, T., et al., Biochemistry, 32, pp. 827-832, 1993) or derivatives thereof (carboxy-PTIO which has carboxyl group introduced at the para-position of the phenyl group of PTIO and the like), triphenylphosphine oxide, triethylamine oxide or the like can be used.

Among the oxide compounds mentioned above, PTIO and derivatives thereof (e.g., carboxy-PTIO) are particularly preferred compounds, and they can be readily obtained by those skilled in the art (listed in, for example, Organic Chemicals Catalog, 32, 1994, Tokyo Kasei Co., Ltd.). The oxide compounds, per se, may be used as a reaction agent, or those encapsulated in liposomes or other may also be used. An amount of the oxygen source is not particularly limited. A preferable amount may be at least 1 μmol or more, preferably 10 to 30 μmol, and more preferably about 10 to 20 μmol, based on nitrogen monoxide to be measured. For the measurement of a sample from a living body, from about 10 to 20 μmol of the oxygen source may preferably be added to the samples. A required amount of the oxygen source is generally supplied by dissolved oxygen. If the amount of oxygen source is extremely small, measuring sensitivity may sometimes be lowered, and if an extremely large amount of oxygen source exists, emission of fluorescence may be disadvantageously affected. Therefore, it is preferred that an amount of nitrogen monoxide to be measured is predicted by a preliminary experiment or a known method so that the oxygen source within an appropriate concentration range can be added. The reaction can be carried out at a temperature of from 10 to 25° C. In addition, the method for measurement of nitrogen monoxide by using a fluorescent probe is described in detail in Tetsuo Nagano et al., "Kagaku to Kyoiku (Chemistry and Education)", 47, pp. 665-669, 1999, and the like, and therefore those skilled in the art can measure nitrogen monoxide with high sensitivity by using the compounds of the present invention by referring to the aforementioned publication.

EXAMPLES

The present invention will be more specifically explained with reference to the examples. However, the scope of the present invention is not limited to the following examples.

Example 1

(1) 4-Acetamido-3-nitrobenzaldehyde

A mixed acid was prepared by adding fuming nitric acid (1 mL), which was added 3 times as divided portions, to concentrated sulfuric acid (6 mL) under ice cooling, and added portionwise with 4-acetamidobenzaldehyde (1.91 g, 11.7 mmol). After the addition, the reaction mixture was immediately poured onto ice, and the solids were collected by filtration. The solids were sufficiently washed with cold water, dried, purified by silica gel column chromatography (developing solvent: $CH_2Cl_2$), and then recrystallized from water to obtain the target compound as pale yellow needlelike solid (1.57 g, yield: 64%).

$^1$H-NMR (300 MHz, $CDCl_3$)
2.36 (3H, s), 8.16 (1H, dd, J=8.79, 1.65 Hz), 8.74 (1H, d, J=1.65 Hz), 9.04 (1H, d, J=8.79 Hz), 9.99 (1H, S), 10.63 (1H, S)
MS (EI): 208 ($M^+$)
m.p.: 156° C.

(2) 4-Amino-3-nitrobenzaldehyde

4-Acetamido-3-nitrobenzaldehyde (2.08 g, 10 mmol) was dissolved in methanol (200 mL). The solution was added with aqueous 2 N HCl (50 mL), and refluxed by heating at 80° C. for 8 hours under an argon flow. The reaction mixture was concentrated under reduced pressure to remove the methanol, and the residue was made basic with aqueous 2 N NaOH, and extracted 5 times with dichloromethane. The organic phases were combined, dried over anhydrous $Na_2SO_4$, and concentrated under reduced pressure to obtain the target compound as yellow solid (1.62 g, yield: 98%).

$^1$H-NMR (300 MHz, $CDCl_3$)
6.91 (1H, d, J=8.58 Hz), 7.92 (1H, dd, J=8.58, 2.01 Hz), 8.63 (1H, d, J=2.01 Hz), 9.82 (1H, s)
MS (EI): 166 ($M^+$)

(3) 3-(2-Methoxycarbonylethyl)-2,4-dimethylpyrrole

Methyl 5-(benzyloxycarbonyl)-2,4-dimethyl-3-pyrrolepropionate (3.1 g, 9.8 mmol) was dissolved in acetone (100 mL). This solution was added with 10% Pd—C, and stirred at room temperature under hydrogen gas. When the starting material disappeared, the reaction mixture was filtered, and the filtrate was distilled under reduced pressure.

The residue was added with trifluoroacetic acid (10 mL), and heated at 40° C. for 10 minutes under an argon flow. The reaction mixture was added with chloroform, and washed once with water, and the aqueous layer was extracted twice with chloroform. The organic phases were combined, washed once with aqueous $Na_2CO_3$ and once with water, dried over anhydrous $Na_2SO_4$, and concentrated under reduced pressure. The residue was purified by silica gel column chromatography (developing solvent: $CH_2Cl_2$) to obtain the target compound as brown liquid (1.6 g, yield: 90%).

$^1$H-NMR (300 MHz, $CDCl_3$)
2.03 (3H, d, J=0.90 Hz), 2.18 (3H, s), 2.45 (2H, m), 2.72 (2H, m), 3.67 (3H, s), 6.38 (1H, d, J=0.90 Hz), 7.53 (1H, s)
MS (EI): 181 ($M^+$)

(4) 6-(4-Amino-3-nitrophenyl)-4,4'-bis(2-methoxy-carbonylethyl)-3,3',5,5'-tetramethylpyrromethene 4-Amino-3-nitrobenzaldehyde (760 mg, 4.58 mmol) and 3-(2-methoxycarbonyl-ethyl)-2,4-dimethylpyrrole (1.6 g, 9.16 mmol) were dissolved in dichloromethane (250 mL). This solution was added with several drops of trifluoroacetatic acid under an argon flow, and stirred overnight at room temperature with shielding from light. After disappearance of the starting materials was confirmed by thin layer chromatography (developing solvent: dichloromethane, silica gel), the reaction mixture was added with 120 mL of a solution of dichlorodicyanoparabenzoquinone (DDQ, 1.07 g, 4.58 mmol) in dichloromethane. The reaction mixture was stirred for 15 minutes, then washed once with water, dried over anhydrous $MgSO_4$, and concentrated under reduced pressure. The residue was purified by alumina column chromatography (developing solvent: methanol/dichloromethane=1/20) to obtain the target compound (yield: 76%).

$^1$H-NMR (300 MHz, $CDCl_3$)
1.37 (6H, s), 2.33 (6H, S), 2.36 (4H, dd, J=8.43, 7.14 Hz), 2.63 (4H, dd, J=8.43, 7.14 Hz), 3.65 (6H, S), 6.32 (2H, S), 6.92 (1H, d, J=8.61 Hz), 7.26 (1H, dd, J=8.61, 2.01 Hz), 8.06 (1H, d, J=2.01 Hz)
MS (EI): 508 ($M^+$)

(5) 8-(4-Amino-3-nitrophenyl)-4,4-difluoro-2,6-bis(2-methoxycarbonylethyl)-1,3,5,7-tetramethyl-4-bora-3a,4a-diaza-s-indacene 6-(4-Amino-3-nitrophenyl)-4,4'-bis(2-methoxycarbonylethyl)-3,3,5,5'-tetramethylpyrromethene (213 mg, 0.42 mmol) was dissolved in dichloromethane (20 mL). The solution was added with diisopropylethylamine (DIEA, 1 mL, 5.7 mmol) under an argon flow, and stirred at room temperature for 10 minutes. The solution was further added with boron trifluoride diethyl etherate (1 mL, 7.9 mmol), and stirred for 40 minutes. A little after the addition, fluorescence appeared. After completion of the reaction, the reaction mixture was washed once with water and twice with aqueous 2 N NaOH, and the aqueous layer and the NaOH layer were combined, and extracted 3 times with dichloromethane. The organic phases were combined, dried over anhydrous $Na_2SO_4$, and concentrated under reduced pressure, and the residue was purified by alumina column chromatography (developing solvent: methanol/dichloromethane=1/20) to obtain the target compound as orange solid (72 mg, yield: 31%).

$^1$H-NMR (300 MHz, $CDCl_3$)
1.46 (6H, s), 2.37 (4H, dd, J=8.25, 7.32 Hz), 2.54 (6H, S), 2.65 (4H, dd, J=8.25, 7.32 Hz), 3.66 (6H, S), 6.32 (2H, S), 6.99 (1H, d, J=8.40 Hz), 7.24 (1H, dd, J=8.40, 1.83 Hz), 8.06 (1H, d, J=1.83 Hz)
MS (EI): 556 ($M^+$)

(6) 8-(4-Amino-3-nitrophenyl)-2,6-bis(2-carboxy-ethyl)-4,4-difluoro-1,3,5,7-tetramethyl-4-bora-3a,4a-diaza-s-indacene 8-(4-Amino-3-nitrophenyl)-4,4-difluoro-2,6-bis(2-methoxycarbonylethyl)-1,3,5,7-tetramethyl-4-bora-3a,4a-diaza-s-indacene (182.5 mg, 0.33 mmol) was dissolved in methanol (100 mL), and this solution was added with aqueous 0.2N NaOH (10 mL), and refluxed by heating at 80° C. for 1 hour. The reaction mixture was concentrated under reduced pressure to remove the methanol, made acidic with aqueous 2 N HCl, and extracted 3 times with ethyl acetate. The organic phases were combined, dried over anhydrous $Na_2SO_4$, and concentrated under reduced pressure. The residue was purified by silica gel column chromatography (developing solvent: methanol/dichloromethane=1/10) to obtain the target compound (87.1 mg, yield: 50%).

$^1$H-NMR (300 MHz, $CD_3OD$)
1.44 (6H, s), 2.26 (4H, dd, J=7.86, 7.32 Hz), 2.40 (6H, S), 2.57 (4H, dd, J=7.86, 7.32 Hz), 7.07 (1H, d, J=8.61 Hz), 7.17 (1H, dd, J=8.61, 2.01 Hz), 7.88 (1H, d, J=2.01 Hz)
MS (FAB): 528 ($M^+$)

(7) 8-(3,4-Diaminophenyl)-2,6-bis(2-carboxyethyl)-4,4-difluoro-1,3,5,7-tetramethyl-4-bora-3a,4a-diaza-s-indacene (p-DAMBO-$P^H$)

8-(4-Amino-3-nitrophenyl)-2,6-bis(2-carboxyethyl)-4,4-difluoro-1,3,5,7-tetramethyl-4-bora-3a,4a-diaza-s-indacene (87.1 mg, 0.16 mmol) was dissolved in methanol (100 mL), and this solution was added with 10% Pd—C, and stirred at room temperature under hydrogen gas. After disappearance of the starting material was confirmed, the reaction mixture was filtered, and the filtrate was distilled under reduced pressure. The residue was purified by silica gel column chromatography (developing solvent: $H_2O$/acetonitrile=1/10) to obtain the target compound as brown solid (31.5 mg, yield: 38%).

$^1$H-NMR (300 MHz, $CD_3OD$)
1.51 (6H, s), 2.28 (4H, dd, J=8.40, 7.14 Hz), 2.47 (6H, S), 2.64 (4H, dd, J=8.40, 7.14 Hz), 6.46 (1H, dd, J=7.86, 2.01 Hz), 6.59 (1H, d, J=2.01 Hz), 6.83 (1H, d, J=7.86 Hz)
MS (FAB): 498 ($M^+$)

(8) 8-(5-Benzotriazolyl)-2,6-bis(2-carboxyethyl)-4,4-difluoro-1,3,5,7-tetramethyl-4-bora-3a,4a-diaza-s-indacene (p-DAMBO-$P^H$-T)

p-DAMBO-$P^H$ (17.4 mg, 0.035 mmol) was added with aqueous 1 N HCl (20 mL), and this solution was added portionwise with aqueous $NaNO_2$ (2.5 mg, 0.036 mmol) with stirring under ice cooling. After completion of the addition, the reaction mixture was returned to room temperature, and stirred for 15 minutes. The solution was extracted 3 times with ethyl acetate. The organic phases were combined, dried over anhydrous $Na_2SO_4$, and concentrated under reduced pressure. The residue was purified by silica gel column chromatography (developing solvent: $H_2O$/acetonitrile=1/10) to obtain the target compound as dark reddish brown solid (14.6 mg, yield: 82%).

$^1$H-NMR (300 MHz, $CD_3OD$)
1.24 (6H, s), 2.30 (4H, dd, J=8.25, 7.14 Hz), 2.51 (6H, S), 2.63 (4H, dd, J=8.25, 7.14 Hz), 7.43 (1H, d, J=8.43 Hz), 7.89 (1H, s), 8.08 (1H, d, J=8.43 Hz)
MS (FAB): 509 ($M^+$)

(9) 8-(3,4-Diaminophenyl)-4,4-difluoro-2,6-bis(2-methoxycarbonylethyl)-1,3,5,7-tetramethyl-4-bora-3a,4a-diaza-s-indacene (p-DAMBO-P$^{Me}$)

8-(4-Amino-3-nitrophenyl)-4,4-difluoro-2,6-bis(2-methoxycarbonylethyl)-1,3,5,7-tetramethyl-4-bora-3a,4a-diaza-s-indacene (131 mg, 0.24 mmol) was dissolved in dichloromethane (50 mL), and further added with methanol (100 ml). This solution was added with 10% Pd—C, and stirred overnight at room temperature under hydrogen gas. After disappearance of the starting materials was confirmed by alumina TLC (developing solvent: dichloromethane), the reaction mixture was filtered, and the filtrate was concentrated under reduced pressure. The residue was purified by alumina column chromatography (developing solvent: dichloromethane, 85 mg, yield: 68%), and recrystallized from hexane/chloroform.

$^1$H-NMR (300 MHz, CDCl$_3$)
1.44 (6H, s), 2.35 (4H, dd, J=8.61, 7.32 Hz), 2.53 (6H, S), 2.64 (4H, dd, J=8.61, 7.32 Hz), 3.46 (2H, S), 3.54 (2H, S), 3.66 (6H, S), 6.55 (1H, d, J=6.39 Hz), 6.56 (s, 1H), 6.79 (1H, d, J=6.39 Hz)
MS (ESI): 549 ([M+Na]$^+$)

Example 2

Test Examples (a) Fluorescence spectrum

The fluorescence characteristics of Compound (7) and Compound (8) were measured. The quantum yield was measured by using F-4500 (Hitachi), and the other spectra were measured by using LS50B (Perkin Elmer). The measurement was performed at 20° C. for a solution of a sample dissolved in 0.1 M sodium phosphate buffer (pH 7.4) using dimethyl sulfoxide of less than 0.2% as a cosolvent. The quantum yield was calculated relative to that of fluorescein, which was 0.85 in aqueous 0.1 M NaOH. The results are shown in Table 1. When similar quantum yield measurements were performed for a compound of the formula (I) wherein R$^6$ and R$^9$ were hydrogen atoms (p-DAMBO) and a compound of the formula (II) wherein R$^{16}$ and R$^{19}$ were hydrogen atoms (p-DAMBO-T) as controls, the quantum yields were 0.001 and 0.40, respectively. Accordingly, the compounds of the present invention were found to successfully give a large quantum yield. Moreover, the Stokes shift of the compounds of the present invention was 16 nm, which was larger than those of p-DAMBO and p-DAMBO-T, namely, a large Stokes shift almost comparable to that of fluorescein was obtained (both the Stokes shifts of p-DAMBO and p-DAMBO-T were 9 nm).

TABLE 1

| Compound | Extinction maximum (nm) | Extinction coefficient (×10$^4$ M$^{-1}$ cm$^{-1}$) | Emission maximum (nm) | Relative quantum yield |
|---|---|---|---|---|
| p-DAMBO-P$^H$ | 519 | 5.8 | 535 | 0.002 |
| p-DAMBO-P$^H$-T | 521 | 5.6 | 537 | 0.74 |

(b) Reaction with Nitrogen Monoxide

Figure 2:
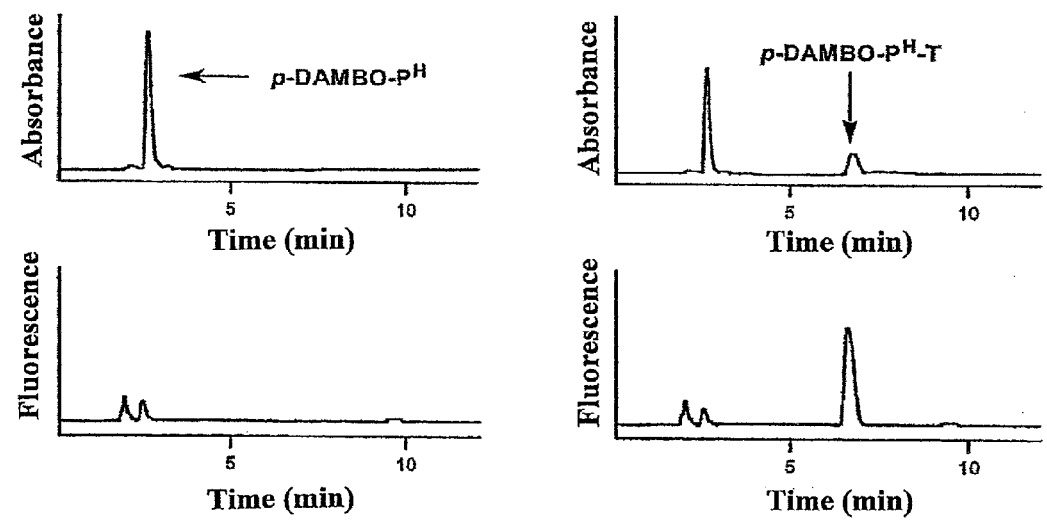
FIG. 2 shows the results of HPLC measurement of the reaction product obtained by adding NOC 13 to Compound (7).

NOC 13, which is a nitrogen monoxide generating agent, was added to Compound (7), and changes of excitation and fluorescence emission spectra were measured. The compound (7) at 5 µM (cosolvent: 0.1% DMSO) and NOC 13 were incubated at 37° C. for 1 hour in 0.1 M sodium phosphate buffer (pH 7.4), and then excitation and fluorescence spectra were measured. The measurement was performed with slit widths of Ex/Em=2.5/2.5 nm, excitation wavelength of 520 nm, and emission wavelength of 535 nm. The results are shown in FIG. 1. Increase of fluorescence depending on the concentration of added NOC 13 was observed. The results obtained by incubating Compound (7) at 5 µM (cosolvent: 0.1% DMSO) and NOC 13 (20 at 37° C. for 1 hour in 0.1 M sodium phosphate buffer (pH 7.4) and then analyzing the product by HPLC are shown in FIG. 2. The HPLC conditions were as follows: column: Inertsil ODS-3 (4.6×250 mm), eluent: aqueous 0.1% H$_3$PO$_4$/acetonitrile=55/45 (v/v), detection: UV-vis (520 nm)/emission (520/535 nm), flow rate: 1 mL/min, and sample volume: 5 µL. Occurrence of extremely rapid reaction of Compound (7) and nitrogen monoxide was observed.

(c) The effect of pH on the Fluorescence Intensity

Figure 3:
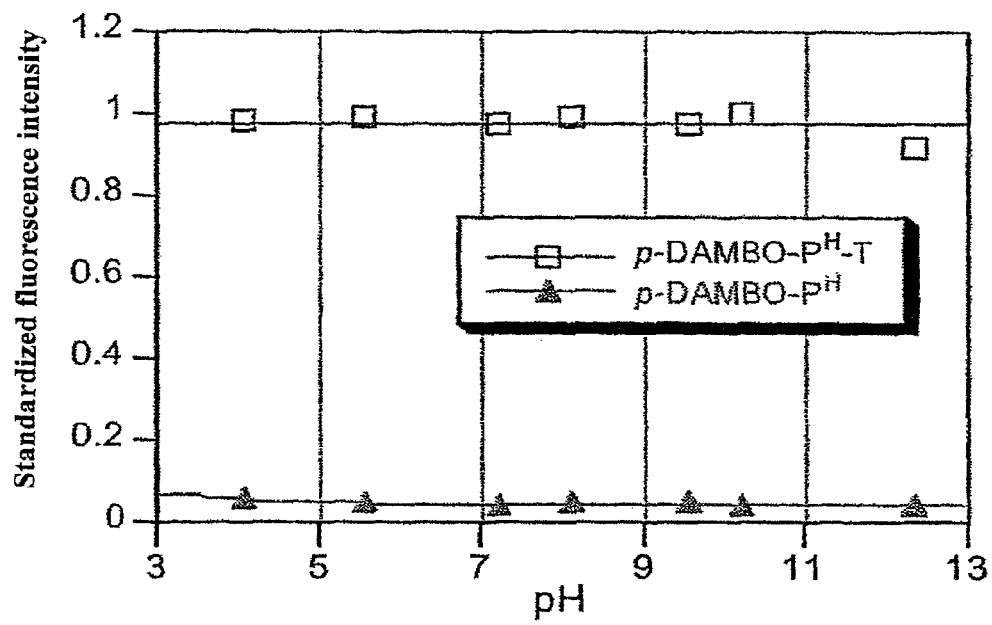
FIG. 3 shows the results of measurement of fluorescence intensity of Compounds (7) and (8) at various pH values.

Compounds (7) and (8) were dissolved in 0.1 M sodium phosphate buffer (cosolvents 0.1% DMSO) adjusted to various pH values, and fluorescence was measured in the same manner as those in the aforementioned (b). The results are shown in FIG. 3. Almost no change in the fluorescence intensity of Compound (8) was observed in an extremely wide pH range of from 3 to 13. Therefore, according to the measurement of nitrogen monoxide by using the compound of the present invention, extremely high accuracy of the measurement is achieved for a biosample with pH fluctuation.

(d) Change in Fluorescence Caused by a Reaction of Compound (9)

Figure 4:
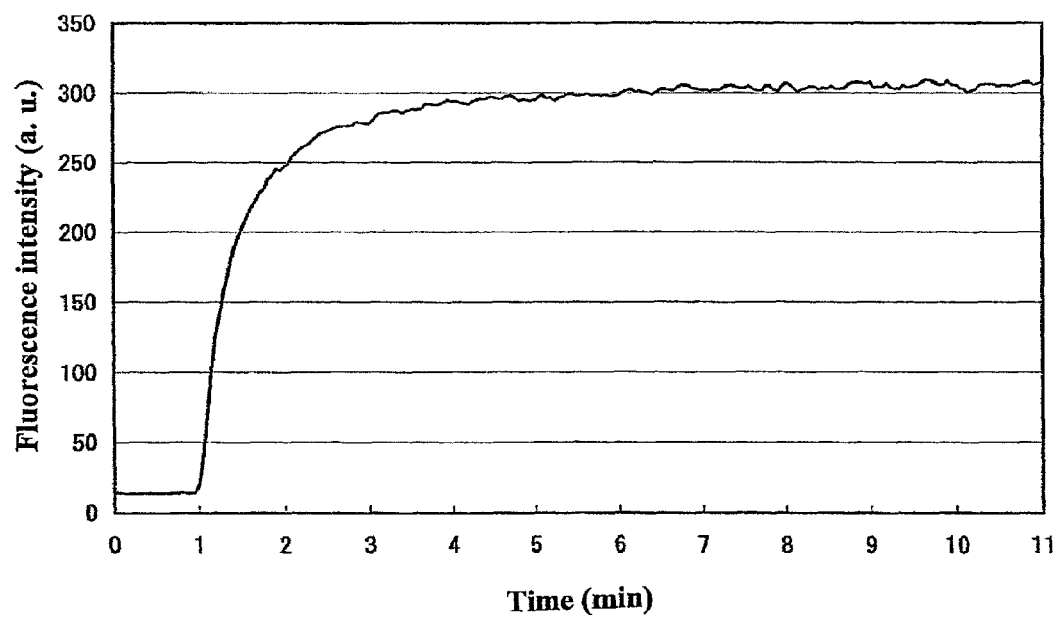
FIG. 4 shows changes of fluorescence intensity observed when a solution of NO in chloroform was added to a solution of Compound (9) in chloroform.

(p-DAMBO-P$^{Me}$) with NO in an organic solvent was measured. A solution of DAMBO-P$^{Me}$ at 1 µM in chloroform was added with 5 µL/minute of a solution of NO in chloroform (prepared by bubbling argon gas in chloroform for 10 minutes and then bubbling NO gas in the same for 3 minutes), and the measurement was performed for 10 minutes. The measurement was performed with slit widths of Ex/Em=5.0/0 nm, excitation wavelength of 520 nm, and emission wavelength of 535 nm. The results are shown in FIG. 4. FIG. 4 shows that measurement of NO in an organic solvent is also possible by using p-DAMBO-P$^{Me}$. From the result, it can be understood that the compound of the present invention has cell membrane permeability, and achieves efficient detection of NO even in a liposoluble environment such as biomembranes.

What is claimed is:
1. A compound represented by the following formula (I):

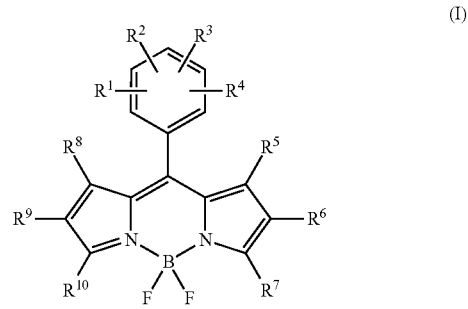

wherein, R$^1$ and R$^2$ represent amino groups that substitute at adjacent positions on the benzene ring, wherein one of the amino groups may have one alkyl group which may be substituted; R$^3$ and R$^4$ independently represent hydrogen atom, a C$_{1-6}$ alkyl group, or a C$_{1-6}$ alkoxy group, R$^5$ and R$^8$ independently represent a C$_{1-6}$ alkyl group which may be substituted, R$^6$ and R$^9$ independently represent a carboxy-substituted C$_{1-6}$ alkyl group, an alkoxycarbonyl-substituted C$_{1-6}$ alkyl group, a sulfo-substituted C$_{1-6}$ alkyl group, or an alkyl sulfonate-substituted C$_{1-6}$ alkyl group, and R$^7$ and R$^{10}$ independently represent a C$_{1-6}$ alkyl group which may be substituted, an aryl group which may be substituted, a C$_{1-6}$ alkoxycarbonyl group which may be substituted, a vinyl group which may be substituted, a thienyl group which may be substituted, or a pyrrolyl group which may be substituted, or a salt thereof.

2. The compound or a salt thereof according to claim 1, wherein $R^6$ and $R^9$ are 2-carboxy-1-ethyl groups, and $R^5$, $R^7$, $R^8$, and $R^{10}$ are methyl groups.

3. The compound or a salt thereof according to claim 1, wherein $R^6$ and $R^9$ are 2-methoxycarbonyl-1-ethyl groups, and $R^5$, $R^7$, $R^8$, and $R^{10}$ are methyl groups.

4. An agent for measurement of nitrogen monoxide comprising the compound or a salt thereof according to claim 1.

5. A method for measurement of nitrogen monoxide, which comprises the steps of:
   (a) reacting a compound represented by the formula (I) according to claim 1 with nitrogen monoxide; and
   (b) detecting a compound represented by the following formula (II):

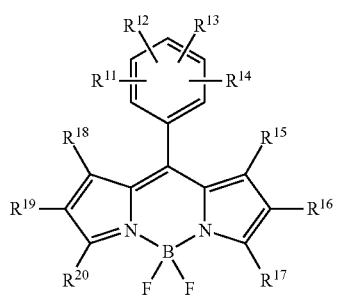

(II)

wherein, $R^{11}$ and $R^{12}$ combine together to represent a group represented by —N=N—NR$^{30}$-which forms a ring structure at adjacent positions on the benzene ring wherein $R^{30}$ represents hydrogen atom, or an alkyl group which may be substituted, or $R^{11}$ and $R^{12}$ represent a combination of an amino group (which may have an alkyl group which may be substituted or a protective group for amino group) and nitro group that substitute at adjacent positions on the benzene ring; $R^{13}$ and $R^{14}$ independently represent hydrogen atom, a $C_{1-6}$ alkyl group, or a $C_{1-6}$ alkoxy group, $R^{15}$ and $R^{18}$ independently represent a $C_{1-6}$ alkyl group which may be substituted, $R^{16}$ and $R^{19}$ independently represent a carboxy-substituted $C_{1-6}$ alkyl group, an alkoxycarbonyl-substituted $C_{1-6}$ alkyl group, a sulfo-substituted $C_{1-6}$ alkyl group, or an alkyl sulfonate-substituted $C_{1-6}$ alkyl group, and $R^{17}$ and $R^{20}$ independently represent a $C_{1-6}$ alkyl group which may be substituted, an aryl group which may be substituted, a $C_{1-6}$ alkoxycarbonyl group which may be substituted, a vinyl group which may be substituted, a thienyl group which may be substituted, or a pyrrolyl group which may be substituted, or a salt thereof.

6. An agent for measurement of nitrogen monoxide comprising the compound or a salt thereof according to claim 2.

7. An agent for measurement of nitrogen monoxide comprising the compound or a salt thereof according to claim 3.

* * * * *